(12) United States Patent
Khizroev et al.

(10) Patent No.: US 11,110,052 B2
(45) Date of Patent: Sep. 7, 2021

(54) 3D NAVIGATION OF NANOPARTICLES VIA INDUCTION OF METASTABLE DIAMAGNETIC RESPONSE

(71) Applicants: Sakhrat Khizroev, Miami, FL (US); Tiffanie Stewart, Miami, FL (US); Abhignyan Nagesetti, Miami, FL (US)

(72) Inventors: Sakhrat Khizroev, Miami, FL (US); Tiffanie Stewart, Miami, FL (US); Abhignyan Nagesetti, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 308 days.

(21) Appl. No.: 16/417,898

(22) Filed: May 21, 2019

(65) Prior Publication Data
US 2020/0085730 A1 Mar. 19, 2020

Related U.S. Application Data

(63) Continuation of application No. 16/131,246, filed on Sep. 14, 2018, now Pat. No. 10,300,011.

(51) Int. Cl.
| | |
|---|---|
| *A61K 9/00* | (2006.01) |
| *A61B 5/055* | (2006.01) |
| *A61N 2/00* | (2006.01) |
| *A61B 5/0515* | (2021.01) |
| *A61K 41/00* | (2020.01) |
| *B82Y 5/00* | (2011.01) |
| *A61B 5/00* | (2006.01) |

(52) U.S. Cl.
CPC ............ *A61K 9/0009* (2013.01); *A61B 5/055* (2013.01); *A61B 5/0515* (2013.01); *A61K 41/00* (2013.01); *A61N 2/004* (2013.01); *A61B 5/0042* (2013.01); *A61B 5/4839* (2013.01); *B82Y 5/00* (2013.01)

(58) Field of Classification Search
CPC ..... A61B 5/0042; A61B 5/0515; A61B 5/055; A61B 5/4839; A61K 41/00; A61K 9/0009; A61N 2/004; B82Y 5/00
See application file for complete search history.

(56) References Cited

U.S. PATENT DOCUMENTS

| | | |
|---|---|---|
| 2007/0196281 A1 | 8/2007 | Jin |
| 2014/0079621 A1 | 3/2014 | Armijo |

*Primary Examiner* — Michael T Rozanski
(74) *Attorney, Agent, or Firm* — Saliwanchik, Lloyd & Eisenschenk

(57) ABSTRACT

Methods and devices for three-dimensional navigation of magnetic nanoparticles are provided. A method can comprise introducing high-anisotropy magnetic nanoparticles to a mammal and directing the high-anisotropy magnetic nanoparticles towards a target region of the mammal. Direction control is achieved by subjecting the high-anisotropy magnetic nanoparticles to an alternating signal comprising a uniform magnetic field pulse having a strength greater than a coercivity of the high-anisotropy magnetic nanoparticles and a magnetic gradient pulse having a highest strength that is less than the coercivity of the high-anisotropy magnetic nanoparticles and a location of a lowest strength at the target region of the mammal, and the direction of the uniform magnetic field pulse being in an opposite direction of the magnetic gradient pulse.

20 Claims, 6 Drawing Sheets

3D NAVIGATION OF NANOPARTICLES VIA INDUCTION OF METASTABLE DIAMAGNETIC RESPONSE

CROSS REFERENCE TO RELATED APPLICATION

The present application is a continuation application of U.S. application Ser. No. 16/131,246, filed Sep. 14, 2018, the disclosure of which is hereby incorporated by reference in its entirety, including all figures, tables, and drawings.

STATEMENT OF GOVERNMENT SUPPORT

This invention was made with government support under Grant No. ECCS1408063 and No. 1237818 awarded by National Science Foundation. The government has certain rights in the invention.

BACKGROUND

Three-dimensional (3D) navigation of magnetic nanoparticles can be used for medical applications for targeted drug delivery, cellular stimulation deep in the brain, or high-contrast imaging.

Traditionally, magnetic nanoparticles (ferromagnetic or ferrimagnetic) that are in a non-superparamagnetic or superparamagnetic state are transported in a 3D space via the application of magnetic field gradients. Effectively paramagnetic, these magnetic nanoparticles tend to move in a direction towards the strongest magnetic field value. However, a magnetic field's strength decreases as it moves farther from an effective source. Consequently, according to this traditional approach, the only way to direct magnetic nanoparticles to an arbitrary point in a 3D space is to introduce time as a variable through an image-guided negative feedback loop, (e.g., using magnetic resonance imaging (MRI) or magnetic particle imaging (MPI) to close the loop). In this case, specific magnetic field gradients are applied for the specific period of time required to direct image-guided nanoparticles to a desired location.

Due to the many technical challenges associated with time-controlled image-guided navigation, this approach has severe limitations in both spatial and temporal resolutions. For example, using this approach to navigate magnetic nanoparticles to any point deep in the brain is difficult to achieve even with a 1-mm spatial resolution. For comparison, a spatial resolution on the order of a few microns or better is required to achieve a navigation control at a single-neuron level. With regards to applications in the neurodegenerative disease field, a high-precision navigation control could open a pathway to treating the brain at a single-neuron level and pinpoint treatment of Alzheimer's disease, Parkinson's disease, autism, and many others.

BRIEF SUMMARY

Embodiments of the subject invention relate to the localization of nanoparticles into a point in a three-dimensional (3D) space. This capability can be used in medical fields where targeted delivery at the neuronal level is vital, e.g., for high-precision imaging, targeted drug delivery into selective neurons deep in the brain, wireless deep-brain stimulation for treatment of Parkinson's Disease (PD), neurodegenerative diseases, treatment of glioblastomas, and other cancers with single-cell precision.

Embodiments of the subject invention provide devices and methods for transforming magnetic nanoparticles with a ferromagnetic or ferrimagnetic composition into metastable nanostructures with a negative magnetic susceptibility (metastable diamagnetic nanoparticles) through matching of the magnetic moment relaxation time to the frequency of external magnetic field pulses. As diamagnetic nanoparticles move towards weaker magnetic fields, the metastable diamagnetic nanoparticles can be navigated to any point in a 3D space via the application of magnetic field gradients.

BRIEF DESCRIPTION OF DRAWINGS

FIG. 5($b$) is an image of a trajectory of magnetic nanoparticles moved from point A to point B by applied magnetic field gradient at 0.01 T/cm. FIG. 5($c$) is an image of a trajectory of magnetic nanoparticles moved from point A to point B by applied magnetic field gradient at 0.1 T/cm.

DETAILED DESCRIPTION

The following disclosure and exemplary embodiments are presented to enable one of ordinary skill in the art to make and use the devices and methods for three-dimensional (3D) navigation of magnetic nanoparticles. Various modifications to the embodiments will be readily apparent to those skilled in the art and the generic principles herein may be applied to other embodiments. Thus, the devices and methods related to the 3D navigation of magnetic nanoparticles are not intended to be limited to the embodiments shown, but are to be accorded the widest scope consistent with the principles and features described herein.

Embodiments of the subject invention provide methods to fabricate metastable magnetic nanoparticles with a diamagnetic response that can be directed to a point in 3D space, in which the 3D magnetic field profile reaches its global or local minimum. The coordinates of this minimum magnetic field point can be controlled by adjusting the magnetic field gradients.

Figure 1:
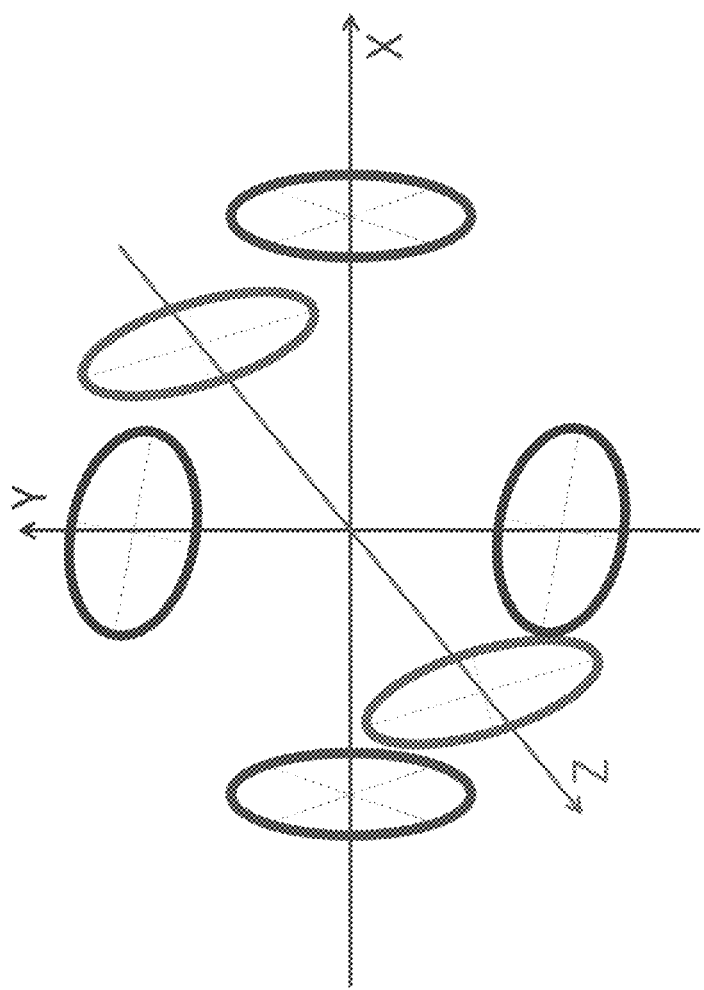
FIG. 1 is a diagram illustrating three sets of electromagnets in the x, y, and z directions.

In one embodiment, to control the location of the minimum magnetic field point in a 3D space, a device can be configured to comprise a set of three pairs of electromagnets positioned along the x, y, and z orientations, respectively, as seen in FIG. 1. In another embodiment, the electromagnets can be arranged in an alternate configuration to suit a particular application. An electromagnet can comprise a conductive wire wrapped in a coil and connected to a current source. Each electromagnetic coil can be wrapped around a magnetic core comprising a ferromagnetic or ferrimagnetic material. Through application of a respective electric current through each electromagnet, a magnetic field can be produced around each electromagnet. The metastable diamagnetic nanoparticles can be directed throughout the 3D space by adjusting the position of the minimum magnetic field point. The location of the minimum magnetic field point is a function of respective electric currents driven through the electromagnets. Therefore, by adjusting the electric currents, the position of the minimum magnetic field point can be changed.

The spatial resolution of the described navigation control method depends on the mechanical stability of electromagnetic coils and the control precision of the electric currents driven through the electromagnetic coils. The device can be configured to have greater than six electromagnetic coils and respective optimization of each of their radii for a particular application. The device can comprise a negative feedback loop through an MRI image-guided control technique or another technique. The optimal values of the electric currents driven through the electromagnetic coils and the resultant magnetic fields can be calculated either analytically or using a commercial software package, such as Comsol, depending on the application.

In one embodiment the device uses a negative feedback loop control system to guide the metastable diamagnetic nanoparticles to follow a desired trajectory and/or towards a desired target location. Based on the image guiding with MRI or magnetic particle imaging (MPI) approach, the controller can readjust the currents through the coils to ensure the nanoparticles move in the right direction.

Embodiments of the subject invention provide methods to fabricate metastable diamagnetic nanoparticles. According to one embodiment, magnetic nanoparticles would be made of a high-anisotropy material, (for example, $L1_0$-phase nanostructures, Co-based iron oxides, etc.).

High-anisotropy materials have a relatively high magnetic anisotropy energy density. Magnetic materials can be divided into soft or hard materials. Hard materials have a relatively high anisotropy energy. The anisotropy energy, whether it is magnetocrystalline, (i.e., due to a relatively strong L-S coupling, or shape-induced), determines certain "easy" orientations in the material along which the magnetic moment prefers to be aligned even without application of an external magnetic field. The higher anisotropy, or in other words, the harder material is, the easier it is for the magnetization to be aligned along the "easy" directions.

For example, a permanent magnet, such as a refrigerator magnet, is made of a high anisotropy material. In turn, the magnetic anisotropy energy reflects a certain magnetic anisotropy field. The anisotropy magnetic field determines the strength of the applied magnetic field required to fully rotate the magnetization direction. In this case, the threshold magnetic field would be defined by the characteristic stray field in the system. Traditionally, materials with an anisotropy field of above approximately 100 Oe are considered as high-anisotropy materials. They can be alloys, polycrystalline, or crystal structures and nanocomposites. High-anisotropy materials can be based on Cobalt (Co), Sm, Nd alloys, Co/Pt or Co/Pd multilayers, $L1_0$-phase structures, alnico, garnets, and many others. In addition, a multi-ferroic material, with the magnetic component made of a high-anisotropy material, could also be used as the material in this application. A dielectric shell in a magnetoelectric nanostructure could further enhance the magnetic anisotropy of the magnetic core because of the interface induced effects.

The high-anisotropy nanoparticles can be subjected to a uniform external magnetic field pulse having a value that exceeds the magnetic coercivity of the high-anisotropy magnetic nanoparticles in a particular orientation. Then a magnetic field gradient pulse having a highest strength that is less than the magnetic coercivity of the high-anisotropy nanoparticles can be applied in the opposite orientation. This causes an intermediate time interval during which the magnetic nanoparticles are effectively diamagnetic.

Figure 2:
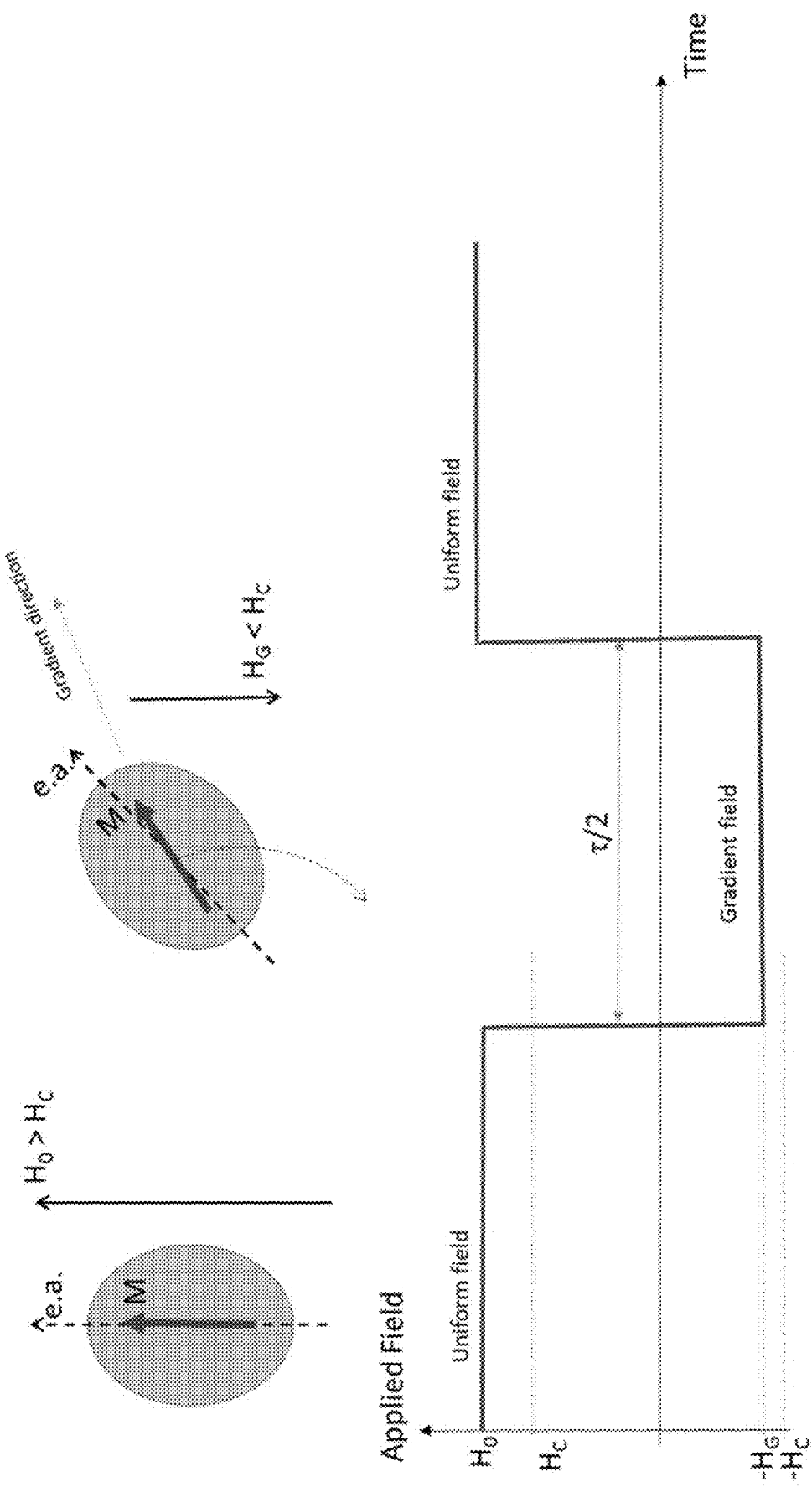
FIG. 2 is a diagram illustrating a high-anisotropy particle's motion under application of a two-step magnetic field cycle.

This intermediate interval can be defined by the time, $\tau$, it takes for the nanoparticles to physically rotate 180 degrees. This time duration is a function of friction force due to the interaction of the high-anisotropy magnetic nanoparticles with their environment (for example, blood, lymph, tissue, etc.). If the intermediate interval time is equivalent to the duration of the magnetic field gradient pulse; and if the two oppositely oriented magnetic fields are applied in an alternating sequence, then the high-anisotropy magnetic nanoparticles will remain in a diamagnetic state and move toward the point with the minimum magnetic field, as illustrated in FIG. 2. During the first half-cycle, a uniform DC magnetic field can be applied to the magnetic nanoparticles with a strength greater than the coercivity of the nanoparticles. During the second half-cycle, a gradient magnetic field in the reverse direction is applied to the magnetic nanoparticles with the maximum value below the coercivity of the magnetic nanoparticles. The half-cycle time is equal to $\tau/2$, where $\tau$ is the time it takes for the nanoparticle to rotate approximately 180° in its environment. The nanoparticle particle simultaneously rotates and moves along the gradient toward the minimum magnetic field point.

In another embodiment, low-anisotropy or superparamagnetic nanoparticles can be guided in 3D space. In contrast to the aforementioned "high-anisotropy" materials, the "low-anisotropy" materials have a relatively low anisotropy energy. Typically, the "low-anisotropy" materials have their anisotropy magnetic field of below approximately 100 Oe. An example of the low-anisotropy material is iron.

Figure 3:
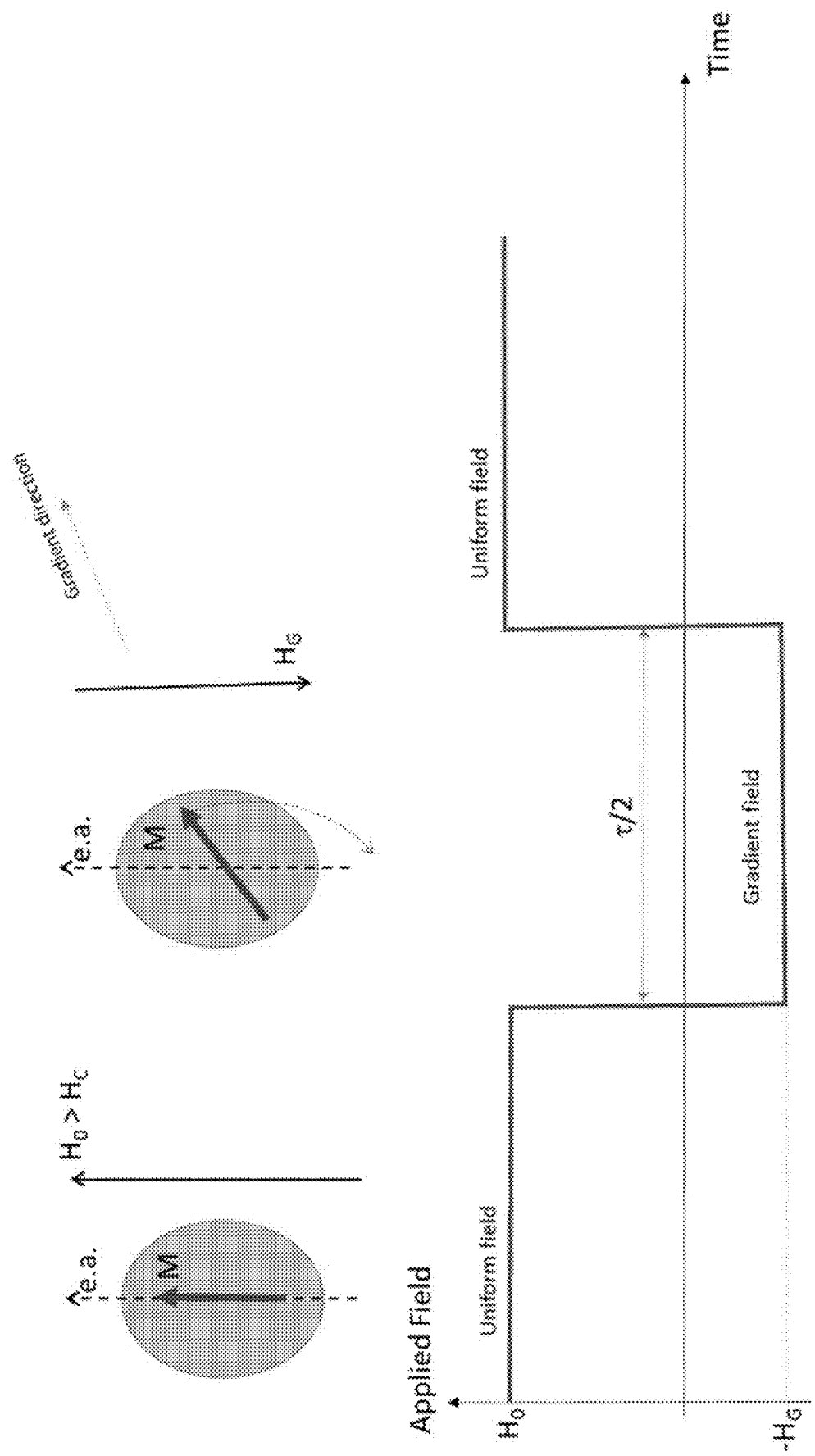
FIG. 3 is a diagram illustrating a low-anisotropy particle's motion under application of a two-step magnetic field cycle.

The magnetic moment of these nanoparticles is relatively weakly whether coupled or not to crystallographic and shape orientations. To create a metastable diamagnetic state with these nanoparticles, the following periodic magnetic field sequence can be applied (see, for example, FIG. 3). During the first half-cycle, an external uniform DC magnetic field is applied with a strength above the coercivity of the nanoparticle. During the second half-cycle, a gradient magnetic field in the reversed direction is applied to the nanoparticles. The maximum value of the gradient magnetic field in the second half-cycle determines the spin relaxation time, $\tau$. The spin relaxation time is the parameter of the nanoparticle, while the intermediate interval time is defined by the external field source. In this embodiment, the respective nanoparticles do not rotate and only move along the gradient of the magnetic field toward the minimum magnetic field point.

During the first half-cycle, the nanoparticles are saturated in one orientation via an application of an external field for a period of time greater than the characteristic spin relaxation time, $\tau$ of the nanoparticle. The magnetic field is then reversed and the nanoparticles are effectively diamagnetic for a period of time less than $\tau$. During this second half-cycle, the applied magnetic field should have a spatial gradient to push the metastable diamagnetic nanoparticles towards the minimum field point. The spin relaxation time significantly increases (by orders of magnitude) as the particle size is reduced below approximately 5 nm and the nanoparticle size can be configured to correlate with a desired spin relaxation time. The spin relaxation time can be as large as 1 millisecond (ms) or even higher. The spin relaxation time is also inversely related to the strength of the applied reversed magnetic field. The greater the strength of the applied reversed magnetic field, the shorter the spin relaxation time. The half-cycles should be maintained with a period defined by the spin relaxation time for the particular strength of the reversed field.

Figure 6:
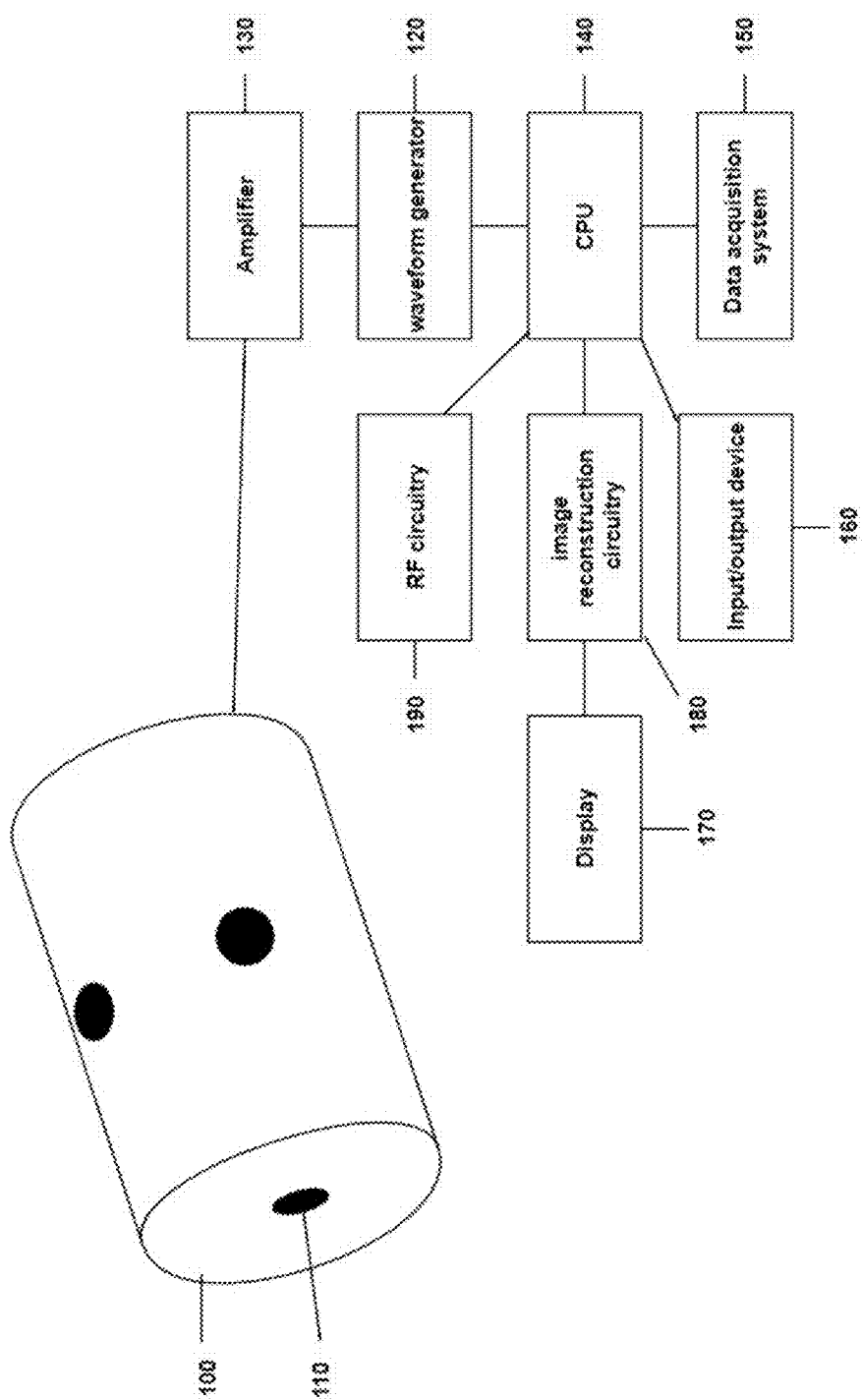
FIG. 6 is a block diagram of a three dimensional navigation system.

FIG. 6 shows a magnetic resonance imaging device utilized to perform the functions described herein. The MRI device 100 comprises a first magnet system (not shown) to generating a steady magnetic field, a second magnet system (each not shown) for generating temporary magnetic gradient fields in three orthogonal directions (x, y, and z). The MRI device 100 comprises an examination space to accommodate a patient or an area of the patient to be examined. RF circuitry 190 comprises an RF transmitter coil 110, for generating RF fields, RF source, an RF receiver coil, and a modulator (not shown). The RF coil 110 is disposed around the examination space of the MM device 100. An RF receiver coil can receive a magnetic resonance signal. In some embodiments, the RF receiver coil is the same coil as the RF transmitter coil. The RF transceiver coil can be connected, to a signal or gradient amplification circuitry and a waveform generator 120. An MM image can be processed by image reconstruction circuitry 180 and displayed on a display 170. Data received from the MRI device 100 can be stored in or retrieved from a data acquisition unit 150. An input/output device 160 can be connected to a central processing unit (CPU) 140 that carries out any provided instructions. The MM device can be configured to modify the magnetic field to direct the local or global minimum to a target region of interest.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the present invention and of the many advantages may be had from the following example, given by way of illustration. The following example is illustrative of some of the methods, applications, embodiments and variants of the present invention. It is, of course, not to be considered as limiting the invention. Numerous changes and modifications can be made with respect to the invention.

Example 1

Figure 4:
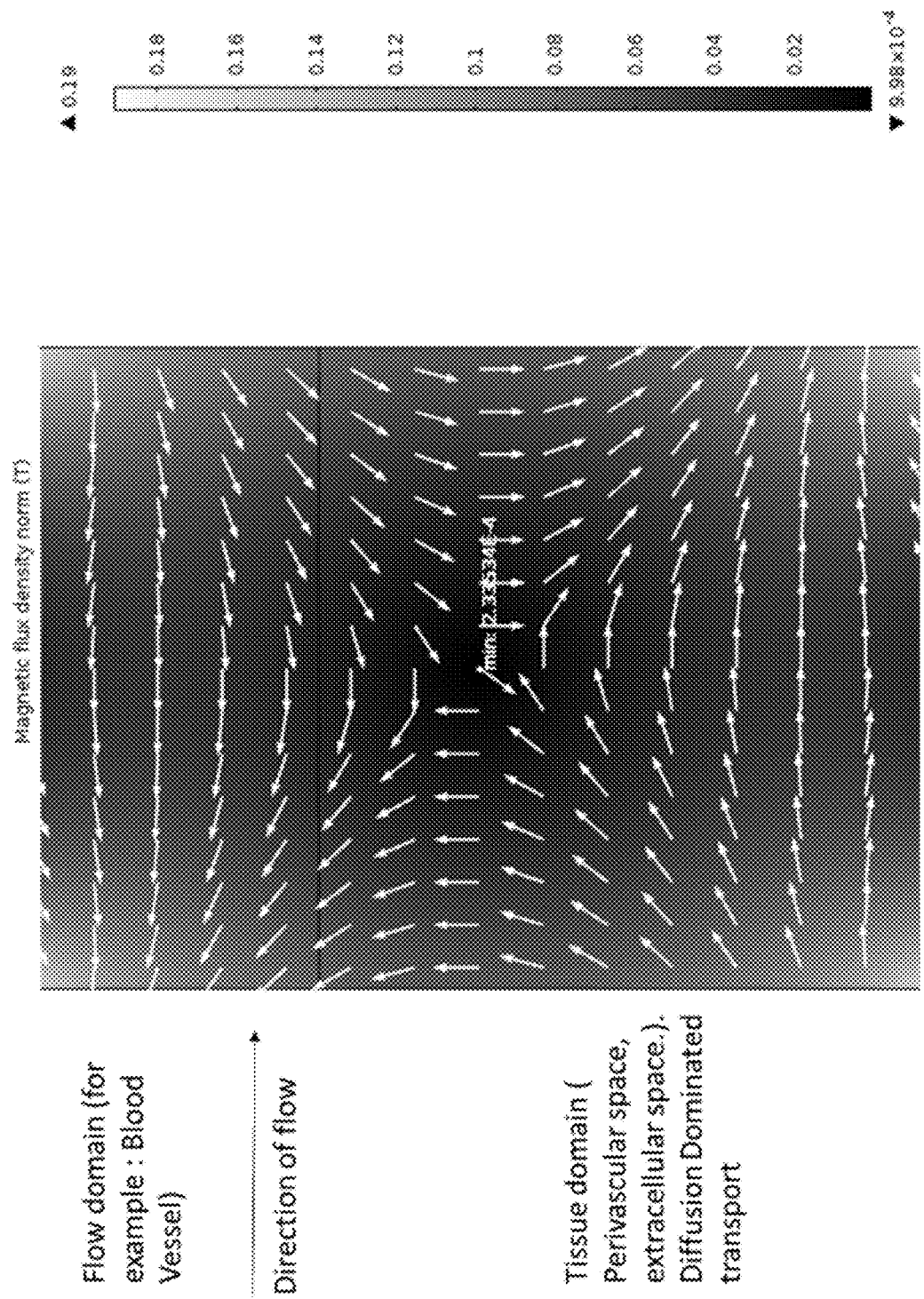
FIG. 4 is a diagram of a magnetic flux profile with a minimum point in the brain's 3D space including a flow domain and a tissue domain.

The herein described methods can be used to navigate magnetic nanoparticles to any point in the brain. The trajectory can be divided into two major domains including (i) brain tissue regions with no flow and (ii) flow regions through the cerebrospinal fluid (CSF) in the brain or blood vasculature outside the brain, respectively. When moving through the CSF or blood currents, in addition to the magnetic force, the nanoparticles experience a force due to the flow dynamic, as illustrated in FIG. 4. When moving through the sponge-like tissue domain, the nanoparticles move with an effective drag coefficient, which in turn strongly depends on the ratio of the average nanoparticle size to the average pore size of the tissue.

Figure 5C:
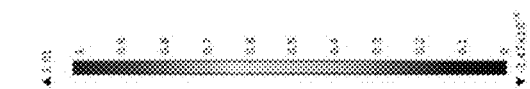
FIG. 5($a$) is an image of a trajectory of magnetic nanoparticles moved from point A to point B by applied magnetic field gradient at 0 T/cm.
Figure 5C:
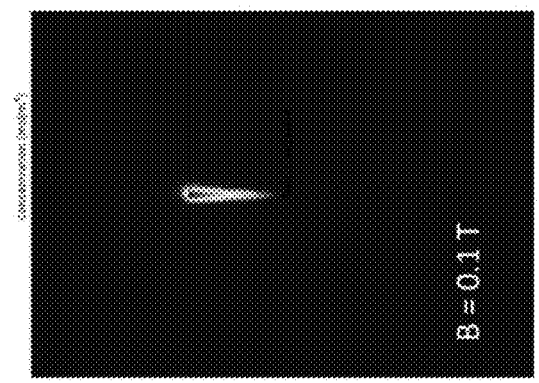
Figure 5B:
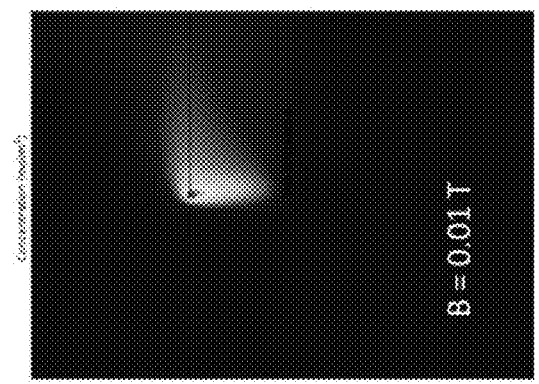
Figure 5A:
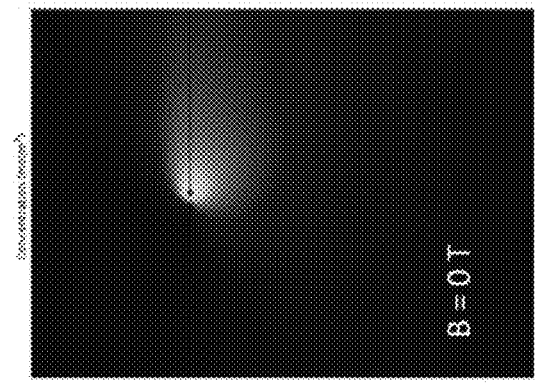

Illustrations in FIG. 5(a)-(c) show Comsol simulation results of trajectories of 30-nm magnetic nanoparticles that were moved from point A to point B separated by 1 cm in the brain via application of specially timed magnetic field gradients. The magnetic field gradients applied were 0, 0.01, and 0.1 T/cm, respectively.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A method of three-dimensional navigation of magnetic nanoparticles, the method comprising:
   introducing low-anisotropy magnetic nanoparticles to a mammal; and
   directing the low-anisotropy magnetic nanoparticles towards a target region of the mammal by:
      subjecting the low-anisotropy magnetic nanoparticles to an alternating signal comprising a uniform magnetic field pulse having a strength greater than a coercivity of the low-anisotropy magnetic nanoparticles and a magnetic gradient pulse having an initial location of a lowest strength at the target region of the mammal,
   the direction of the uniform magnetic field pulse being opposite of the direction of magnetic gradient pulse.

2. The method according to claim 1, further comprising adjusting a spin relaxation time of a low-anisotropy magnetic nanoparticle of the low-anisotropy magnetic nanoparticles comprising adjusting a size of the of the low-anisotropy magnetic nanoparticle.

3. The method according to claim 2, the low-anisotropy magnetic nanoparticles comprising iron.

4. The method according to claim 1, further comprising adjusting a spin relaxation time of a low-anisotropy magnetic nanoparticle comprising adjusting a strength of the magnetic gradient pulse.

5. The method according to claim 4, the low-anisotropy magnetic nanoparticles comprising iron.

6. The method according to claim 1, a time duration of the uniform magnetic field pulse being equal to a time duration of the magnetic gradient pulse.

7. The method according to claim 6, the low-anisotropy magnetic nanoparticles comprising iron.

8. The method according to claim 1, a respective time duration of each of the uniform magnetic field pulse and the magnetic gradient pulse being dependent upon a spin relaxation time at a particular strength of the magnetic gradient pulse.

9. The method according to claim 8, the low-anisotropy magnetic nanoparticles comprising iron.

10. The method according to claim 1, further comprising:
altering a direction of the low-anisotropy magnetic nanoparticles by adjusting the location of the lowest strength of the magnetic gradient pulse.

11. The method according to claim 10, the low-anisotropy magnetic nanoparticles comprising iron.

12. The method according to claim 1, the uniform magnetic field pulse and the magnetic gradient pulse being applied by an electromagnet comprising a conductive wire wrapped in a coil.

13. The method according to claim 12, the conductive wire being wrapped around a magnetic core.

14. The method according to claim 12, the low-anisotropy magnetic nanoparticles comprising iron.

15. The method according to claim 1, the low-anisotropy magnetic nanoparticles comprising iron.

16. The method according to claim 1, a time duration of the uniform magnetic field pulse being equal to a time duration required for the low-anisotropy magnetic nanoparticles to physically rotate 180 degrees inside the mammal.

17. The method according to claim 16, a time duration of the magnetic gradient pulse being equal to the time duration required for the low-anisotropy magnetic nanoparticles to physically rotate 180 degrees inside the mammal.

18. The method according to claim 17, the low-anisotropy magnetic nanoparticles comprising iron.

19. The method according to claim 1, a time duration of the magnetic gradient pulse being equal to a time duration required for the low-anisotropy magnetic nanoparticles to physically rotate 180 degrees inside the mammal.

20. A method of three-dimensional navigation of magnetic nanoparticles, the method comprising:
introducing low-anisotropy magnetic nanoparticles to a mammal; and
directing the low-anisotropy magnetic nanoparticles towards a target region of the mammal by:
subjecting the low-anisotropy magnetic nanoparticles to an alternating signal comprising a uniform magnetic field pulse having a strength greater than a coercivity of the low-anisotropy magnetic nanoparticles and a magnetic gradient pulse having an initial location of a lowest strength at the target region of the mammal,
the direction of the uniform magnetic field pulse being opposite of the direction of magnetic gradient pulse,
adjusting a spin relaxation time of a low-anisotropy magnetic nanoparticle of the low-anisotropy magnetic nanoparticles comprising adjusting a size of the of the low-anisotropy magnetic nanoparticle and a strength of the magnetic gradient pulse,
the low-anisotropy magnetic nanoparticles comprising iron,
a time duration of the uniform magnetic field pulse being equal to a time duration of the magnetic gradient pulse,
the time duration of the uniform magnetic field pulse and the time duration of the magnetic gradient pulse being dependent upon a spin relaxation time at a particular strength of the magnetic gradient pulse,
the method further comprising altering a direction of the low-anisotropy magnetic nanoparticles by adjusting the location of the lowest strength of the magnetic gradient pulse,
the uniform magnetic field pulse and the magnetic gradient pulse being applied by an electromagnet comprising a conductive wire wrapped in a coil,
the conductive wire being wrapped around a magnetic core,
the time duration of the uniform magnetic field pulse being equal to a time duration required for the low-anisotropy magnetic nanoparticles to physically rotate 180 degrees inside the mammal, and
the time duration of the magnetic gradient pulse being equal to the time duration required for the low-anisotropy magnetic nanoparticles to physically rotate 180 degrees inside the mammal.

* * * * *